United States Patent
Barry et al.

(10) Patent No.: US 6,267,590 B1
(45) Date of Patent: Jul. 31, 2001

(54) ANTIMICROBIAL DENTAL PRODUCTS

(75) Inventors: John E. Barry, Derry, NH (US); Jeffrey A. Trogolo; Elizabeth A. Pastecki, both of Boston, MA (US)

(73) Assignee: AgION Technologies, LLC, Wakefield, MA (US)

( * ) Notice: Subject to any disclaimer, the term of this patent is extended or adjusted under 35 U.S.C. 154(b) by 0 days.

(21) Appl. No.: 09/449,224

(22) Filed: Nov. 24, 1999

(51) Int. Cl.$^7$ ........................................ A61C 3/00
(52) U.S. Cl. .................................... 433/8; 433/20
(58) Field of Search ..................... 433/8, 9, 20, 173, 433/201.1, 168.1, 215, 229

(56) References Cited

U.S. PATENT DOCUMENTS

| | | |
|---|---|---|
| 4,412,015 | 10/1983 | Lustgarten et al. . |
| 4,677,143 | 6/1987 | Laurin et al. . |
| 4,775,585 | 10/1988 | Hagiwara et al. . |
| 4,906,464 | 3/1990 | Yamamoto et al. . |
| 4,911,898 | 3/1990 | Hagiwara et al. . |
| 4,911,899 | 3/1990 | Hagiwara et al. . |
| 4,938,955 | 7/1990 | Niira et al. . |
| 4,938,958 | 7/1990 | Niira et al. . |
| 4,946,387 | 8/1990 | Adell . |
| 5,009,898 | 4/1991 | Sakuma et al. . |
| 5,052,926 | 10/1991 | Kawasaki et al. . |
| 5,068,107 | 11/1991 | Hollibush et al. . |
| 5,094,847 | 3/1992 | Yazaki et al. . |
| 5,100,671 | 3/1992 | Maeda et al. . |
| 5,102,401 | 4/1992 | Lambert et al. . |
| 5,141,980 | 8/1992 | Ranceze et al. . |
| 5,180,585 | 1/1993 | Jacobson et al. . |
| 5,189,585 | 2/1993 | Kubo . |
| 5,290,544 | 3/1994 | Shimono et al. . |
| 5,296,238 | 3/1994 | Sugiura et al. . |
| 5,413,788 | 5/1995 | Edwards et al. . |
| 5,441,717 | 8/1995 | Ohsumi et al. . |
| 5,474,797 | 12/1995 | Sioshansi et al. . |
| 5,562,872 | 10/1996 | Watanabe . |
| 5,614,568 | 3/1997 | Mawatari et al. . |
| 5,648,403 | 7/1997 | Martin . |
| 5,681,575 | 10/1997 | Burrell et al. . |
| 5,697,203 | 12/1997 | Niwa . |
| 5,714,430 | 2/1998 | Gehrer et al. . |
| 5,714,445 | 2/1998 | Trinh . |
| 5,716,208 | 2/1998 | Forman . |
| 5,730,995 | 3/1998 | Shirono et al. . |
| 5,753,251 | 5/1998 | Burrell et al. . |
| 5,766,611 | 6/1998 | Shimono et al. . |
| 5,769,638 | 6/1998 | Torabinejad et al. . |
| 5,770,255 | 6/1998 | Burrell et al. . |
| 5,772,436 | 6/1998 | Matsui et al. . |
| 5,795,151 | * 8/1998 | Nonami et al. ................... 433/8 |
| 5,906,466 | 5/1999 | Eandi . |

FOREIGN PATENT DOCUMENTS

| | | |
|---|---|---|
| 63-294607 | * 11/1988 | (JP) . |
| 5-163125 | * 6/1993 | (JP) . |
| 06257046 | * 10/1994 | (JP) . |
| 07081785 | 3/1995 | (JP) . |
| 07300118 | * 11/1995 | (JP) . |
| 07300119 | * 11/1995 | (JP) . |
| 08041611 | * 2/1996 | (JP) . |
| 08142066 | * 6/1996 | (JP) . |

\* cited by examiner

*Primary Examiner*—Nicholas D. Lucchesi
(74) *Attorney, Agent, or Firm*—Steven J. Hultquist; Edward K. Welch, II; Marianne Fuierer

(57) ABSTRACT

A dental appliance, such as of the orthodontic type, to be placed in the mouth and having an inorganic antimicrobial agent on a surface, the agent preferably being a zeolite. The dental appliance may comprise metal or a polymer and the agent may be present in a coating that is applied to the surfaces of the appliance that are to be contacted by liquids or solids in the mouth. The appliance can be of a polymer resin or an elastomer incorporating the agent. A preferred antimicrobial agent is ceramic particles (e.g., zeolite particles) containing antimicrobial metal ions, e.g., silver ions, as the active agent.

21 Claims, 2 Drawing Sheets

ANTIMICROBIAL DENTAL PRODUCTS

FIELD OF THE INVENTION

This invention relates to dental products, such as used for orthodontic purposes, having an inorganic antimicrobial agent.

BACKGROUND OF THE INVENTION

Orthodontic treatment requires the use of appliances such as brackets, arch wires, retainers, braces and other paraphernalia in the mouth. When present in the mouth, these appliances interfere with normal oral hygiene. As a result, the prevention and treatment of oral diseases, such as gingivitis, periodontitis and dental caries, becomes very difficult during a course of orthodontic treatment. The appliances provide locations where food can accumulate and they thereby constitute a source for bacteria growth. Accordingly, it would be desirable to make these types of appliances in a manner such as to prevent the adverse effects of bacterial action.

Various efforts have been made to provide antimicrobial action for medical type products to be implanted into the body has been considered. For example, U.S. Pat. No. 5,906,466 describes an antimicrobial composition comprising antimicrobial silver compounds deposited on a physiologically inert oxide support material. In Japanese Patent Abstract No. 08041611 an alloy exhibiting antimicrobial properties is disclosed. None of these are specifically directed to orthodontic appliances.

Attempts have been made to solve various aspects of this problem in the field of orthodontic appliances. For example, in U.S. Pat. No. 5,068,107 an elastic retainer member, such as formed by an elastic polymeric material, is provided with a dentally active pharmacological agent, such as halide salt and various compositions that contain fluoride. The agent is released in the mouth. Such a product suffers from the defect of the agent being depleted over time, thereby requiring replacement of the appliance. Also, this approach is not easily used for metal orthodontic appliances. U.S. Pat. No. 5,716,208 discloses an orthodontic bracket to be attached to a tooth that has an outer coating that contains an organic antimicrobial agent, the preferred one disclosed being 2,4,4'-trichloro-2'-hydroxy-diphenyl ether (triclosan) which is a halogenated diphenyl ether. Triclosan is an organic compound, and therefore suffers from the disadvantage that antibiotic resistance can develop over time with continued use. Furthermore, triclosan is suspected of inducing skin irritation.

SUMMARY OF THE INVENTION

The present invention is directed to dental appliances, particularly for use in orthodontic applications. The appliances are either of plastic or metal and contain an inorganic antimicrobial agent which imparts substantial antimicrobial action to materials that contact the appliance. In accordance with the invention, preferred inorganic agents are antimicrobial particles (e.g., zeolite particles) containing antimicrobial metal ions (e.g., silver ions), as the active agents. Such zeolites can effect a sustained release of the active component, such as silver, into the mouth cavity over an extended period of time. Zeolites are preferred as the inorganic agent since they are long-lasting and effective even in the environment of the mouth, where there is prolonged contact with saliva. Therefore, the appliances do not have to be replaced to maintain the antimicrobial action, or are replaced less frequently than prior art devices having antimicrobial action.

Where the dental product is formed of a polymeric plastic resin, the antimicrobial agent is mixed with the resin that is used to form the product. The agent also can be mixed with an elastomer to produce an appliance having elastic properties. Alternatively, a coating containing the antimicrobial agent also can be used. In a dental appliance formed of metal, the agent is contained in a coating which is bonded to the product.

The present invention is applicable to various types of orthodontic appliances, such as arch wires and brackets and elastic members such as retainers.

OBJECTS OF THE INVENTION

It is therefore an object of the present invention to provide dental appliances, such as used for orthodontic purposes, containing an antimicrobial agent.

A further object is to provide orthodontic dental appliances formed of plastic or metal which contain a zeolite as an inorganic antimicrobial agent.

Still a further object is to provide orthodontic dental appliances made of metal or plastic in which the antimicrobial zeolite is present in a coating applied to either a plastic or metal product or incorporated into the resin forming the plastic product.

BRIEF DESCRIPTION OF THE DRAWINGS

Other objects and advantages of the present invention will become more apparent upon reference to the following specification and annexed drawings, in which.

DETAILED DESCRIPTION OF THE INVENTION

Antimicrobial Dental Products

Figure 1:
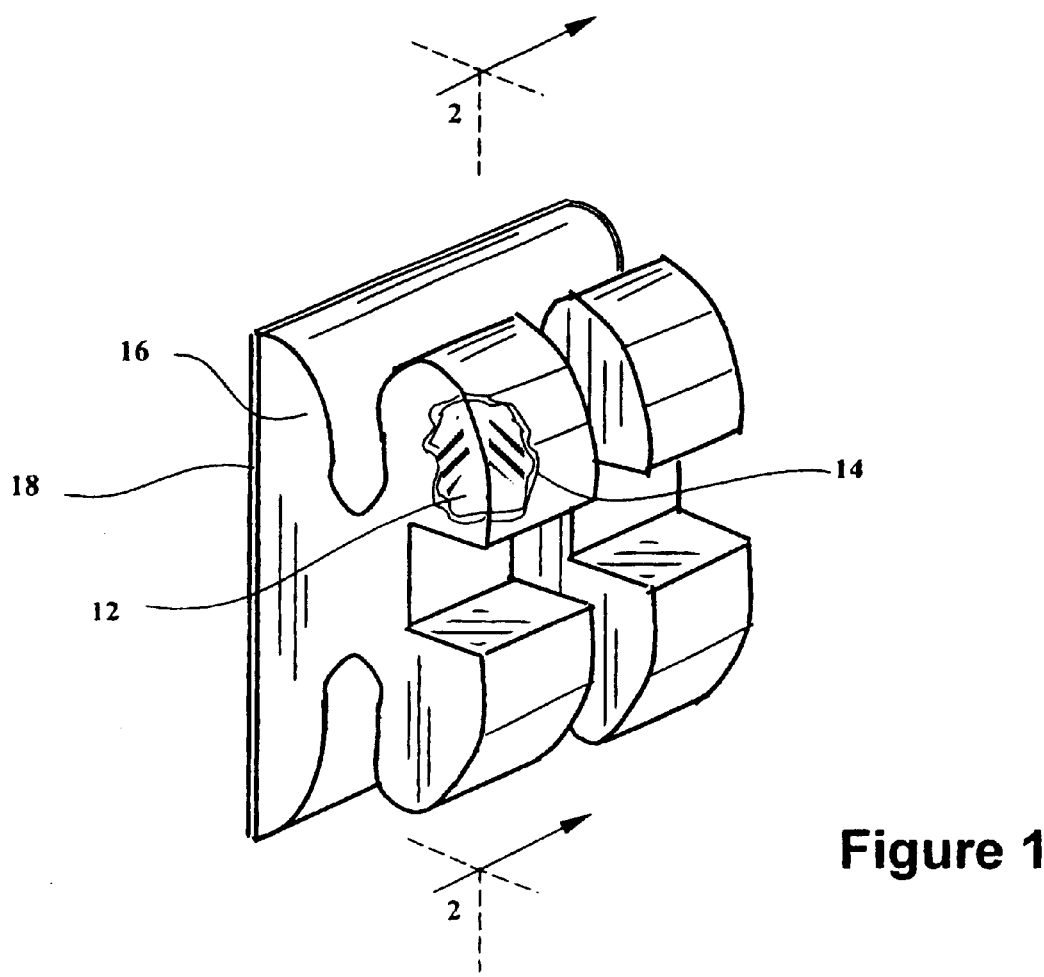
FIGS. 1 and 2 are views of a clamp incorporating the antimicrobial agent in a coating or in the clamp body if made of resin.
Figure 2:
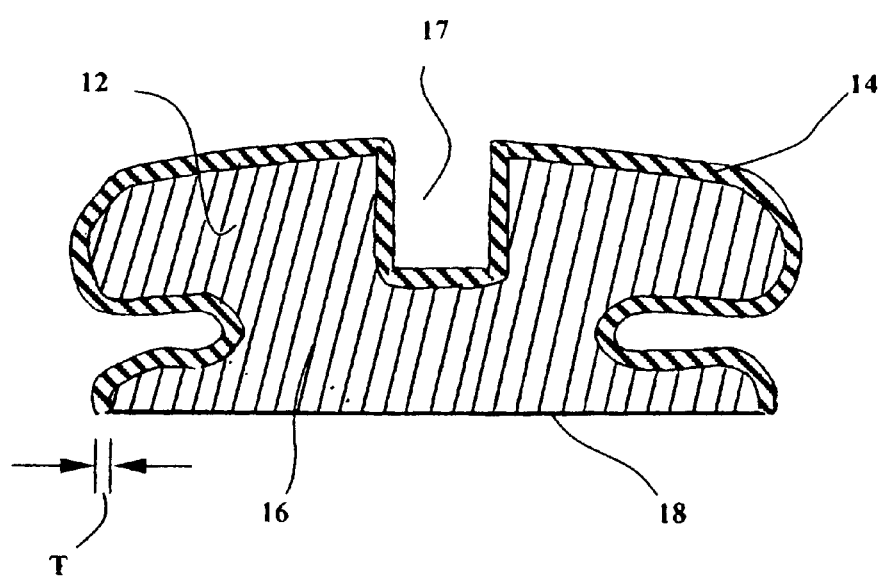

FIGS. 1 and 2 show a type of dental product in which the present invention can be utilized, here an orthodontic bracket. The bracket of these Figures corresponds to that shown in U.S. Pat. No. 5,716,208. The orthodontic bracket 10 consists of a bracket body 12 coated with an outer coating 14. The bracket body 12 can be of any suitable metal, or can be of a translucent or transparent plastic material or any suitable biocompatible metal. These general types of materials are commonly used in the practice of orthodontic care. It should be understood that the size and shape of the bracket body 12 is not critical to the practice of the subject invention, which applies to orthodontic appliances of all types, sizes and mostly all shapes. The bracket is described for purposes of illustration.

The bracket body 12 has a base region 16. The base surface 18 that defines one side of the base region 16 is the surface that abuts against a tooth after the bracket body 12 is applied to the tooth. Although the present embodiment shows a bracket body 12 designed to be adhesively affixed to a tooth, such an embodiment is merely exemplary and it should be understood that bracket bodies designed to mechanically attach to teeth also can be used.

The bracket body 12 has a coating 14 over most of the surface except for the base surface 18 that joins to a tooth. The coating 14 contains the inorganic antimicrobial agent. That is, the particles of the agent are contained in the coating material. Various types of suitable coating materials are discussed below.

In all of the types of orthodontic appliances incorporating the subject invention the antimicrobial agent is present in an effective amount. This means that there is a sufficient amount of the antimicrobial agent added to or combined with other materials, such as the coating material, to be present on the appropriate surfaces of the appliance to impart substantial antimicrobial action on the surface thereof, i.e. to prevent or inhibit the growth of bacterial and/or fungal organisms or to kill such organisms. The amount of the agent will vary based on the specific agent used and the material with which it is mixed or added to and upon known factors such as the moisture content and temperature of the mouth. It is within the ability of one skilled in the art, in view of this disclosure, to relatively easily determine an effective amount of the antimicrobial agent to be used with each material.

In preferred embodiments, the agent particles comprise about 0.1%–100% by weight of the coating material, more preferably between about 0.1%–75% and most preferably between about 0.5%–50.0%. As explained above, an effective amount of the agent is present.

The coating can be applied in several different ways depending upon the material of the appliance. The following are exemplary embodiments of antimicrobial brackets.

Bracket is of resin and has a coating with the agent—here, the bracket body 12 comprises a plastic resin, such as polyethylene, polycarbonate or polyurethane. Polymeric materials are preferred for the coating material for a bracket of this type of material. The polymers can be of an acrylic, silicone rubber, hydrophilic polymers, or mixtures thereof. The coating material is selected to be compatible with the material of the bracket. Particles containing the antimicrobial agent are thoroughly and uniformly mixed with the coating material. For example, zeolite ceramic particles containing antimicrobial metal ions as an active agent can be mixed directly with the coating material. Alternatively, such zeolite particles are often supplied in a resin base, such as of polyethylene, polyurethane and other resins, these type of resin base particles hereafter referred to as pellets. Typically, the original ceramic zeolite particles will be about 20.0 wt. % of the pellets. The pellets are ground or otherwise processed to the desired size and are mixed in the coating material. Where the bracket is formed of resin, the base resin of the zeolite particles is selected to be compatible with the materials of both the bracket and the coating.

The coating 14 containing the agent is applied to the desired surfaces of the bracket by any suitable technique, such as spraying, painting or dipping. Heat may be applied as required. After the coating dries and the bracket is mounted to the tooth, the agent is present on the surface of the bracket to come into contact with any particles of food or other matter trapped by the bracket, and performs its antimicrobial action.

A preferred embodiment of a coated resin bracket is:

| | |
|---|---|
| resin material of bracket | polycarbonate |
| coating material | acrylic |
| agent type | silver zeolite (e.g., Shinagawa AJ10D) |
| size of agent particles | 1.0 micron |
| wt. % of original agent particles in the coating | 35.0–75.0 wt % of the coating |

Bracket is of metal that is coated—where the bracket body 12 is formed of metal, the same type of coating is used as described above for the bracket formed of a plastic resin material. As before, the coating is applied to the desired surface area of the metal bracket by any suitable technique, such as painting or spraying. The surface of the bracket initially can be roughened to enhance the bond of the coating.

The coating may be colored to contrast with the ivory white color of teeth and the pink-red color of gums, the tongue and the inside of the mouth. For instance, the coating 14 can be colored blue, green, black, fluorescent orange, or any other contrasting color. The presence of the coating 14 on the bracket body 12 makes the overall bracket body 12 easy to see when inside the mouth. Since the color of the coating 14 contrasts with the ivory white of the teeth and the pink-red colors of the tongue, mouth and gums, an orthodontic practitioner can easily identify the orthodontic bracket 10 even if it is inadvertently dropped in the mouth during the application procedure. The contrasting color of the outer coating 14 also makes the orthodontic bracket 10 easy to align on the teeth because the edges of the orthodontic bracket 10 are readily discernable and therefore are much easier to align by eye. The use of a colorant in the coating is desirable for various types of appliances.

The liquid or media present in the coating 14 is water insoluble, but is preferably soluble in a suitable solvent. As a result, the coating 14 containing the agent will not ordinarily dissolve into the mouth. Where the coating is colored, the -water insolubility feature prevents the color from running into the mouth and changing the tint of the saliva. The colorant can be any pigmented particle that itself does not readily dissolve in water, and is preferably pigment particles encapsulated within the coating 14. As such, the pigment particles themselves need not be dissolvable in the liquid or media present in the coating. Rather, the pigment particles are rinsed away as the coating 14 dissolves in a solvent rinse. In an alternative embodiment, the colorant can be a color salt.

Bracket is of metal, powder coating—the agent can be applied to a metal bracket body 12 by a powder coating technique. The typical powder coating process usually comprises the basic steps of cleaning the metal, electrostatically spraying the powder onto the object to be coated, and baking. Here, the inorganic antimicrobial agent particles are incorporated into the sprayed coating.

To form the powder for the spray coating, the particles of the agent are blended with the powder to be sprayed. The composite of agent containing particles and the spray powder is ground or melt atomized to produce a powder that is used directly or diluted with untreated spray powder used in the conventional powder coating process. The powder so formed is applied in the normal spray coating manner. The spray coated article is then baked.

The particles of the agent also can be applied in a separate second step to the surface of a powder coated part before the baking step.

Incorporation of the inorganic antimicrobial into the spray powder also can be accomplished by preparing a master batch concentrate of resin based pellets containing the agent particles. The pellets containing the agent particles are processed to the desired size and are blended into the same or a different material for the spray powder to the desired concentration.

An alternate powder coating method is to form a dispersion of an untreated polymer powder with inorganic antimicrobial particles in an appropriate liquid or media to form a dispersion. The dispersion may optionally contain a binder. This coats the inorganic antimicrobial on the polymer powder particles. The liquid or media is then evaporated and the powder which is coated with the agent is used in the conventional powder coating process. This ensures that the inorganic antimicrobial is exposed at the surface of the device.

Another method of producing an antimicrobial powder coating is to apply a powder coating onto the device surface in the conventional manner and then apply a coating of the inorganic antimicrobial in a liquid dispersion. The part is then dried and baked as in the conventional powder coating process, thus incorporating the inorganic antimicrobial specifically into or near the surface of the coating.

In each of the described spray powder coating techniques an effective amount of the agent is used. Typically, the basic ceramic zeolite particles comprise between 0.1 to 30.0 wt %, preferably 0.5 to 15.0 wt %, most preferably 1.0 to 10.0 wt % of the final powder sprayed on the bracket body 12. If desired, the polymer powder used in the spray coating can be colored.

In another embodiment, the bracket body 12 itself is formed of a suitable plastic resin material and the agent is mixed with the resin used to form the bracket in an effective amount to be available over the entire bracket surface. This approach applies to many types of orthodontic appliances made of a polymer.

In the manufacture of the polymer type appliances, as in the coating material for the appliances, the preferred antimicrobial agent is an antimicrobial zeolite containing antimicrobial metal ions (preferably silver ions) incorporated as ceramic particles. Suitable zeolites and a method for incorporating them into a resin is disclosed in U.S. Pat. Nos. 4,938,955 and 4,906,464. The resins can be those such as polyethylene, polypropylene, polystyrene, polyvinyl chloride, polycarbonate, ABS resins, silicones and others disclosed in said patents.

In a typical process for forming the resin material containing the agent used to make appliances such as the bracket, a zeolite is used as the antimicrobial agent. As explained above, zeolites are often obtained in master batch pellets of particles of low density polyethylene, polypropylene, UHMWPE or polystyrene, all containing about 20.0 wt. % of the zeolite particles. Thus, they can be easily mixed with the resins used as thermoplastic materials for forming the composite resin used to make the bracket or other appliance.

For example, in making an orthodontic appliance formed of resin, such as the bracket 12, the master batch resin pellets of the desired size containing the zeolite particles are kneaded into the resin for the appliance. Both of these can be, for example, of polyurethane. The composite of the resin and the resin zeolite particles is then processed in a conventional manner, such as by injection molding, to form the bracket 12 described above or any other appliance. The particles of the agent will be over the entire exposed surface of the bracket as formed. When the bracket 12 is placed on a tooth the agent will be present to react with food particles and other bacteria. Other antimicrobial agents, as described below, are also suitable and would be processed in a manner consistent with the agent and resin used.

The particles of the agent are present in the final resin in an amount of between about 0.1–30.0% and more preferably between about 0.1–5.0% and most preferably between about 0.5–3.0%. The size of the agent zeolite particles is preferably about 1.0 micron and if the agent is the pellet form, the pellets are of a size of between about 3.0–15.0 microns.

A typical bracket of the resin containing the agent is:

| | |
|---|---|
| resin for bracket | polycarbonate |
| agent | zeolite silver (e.g., Shinagawa AJ-10D) |
| agent base resin | polycarbonate |
| size of agent particles | 1.0 micron |
| wt % of agent particles in final resin | 0.5 to 5.0% |

The example given above is specific to a bracket. However, the criteria is applicable to all types of orthodontic appliances of plastic. The molding of said appliances with the agent in the resin or the coating of an appliance formed of metal or a polymer can be used for all types of such appliances.

Figure 3:
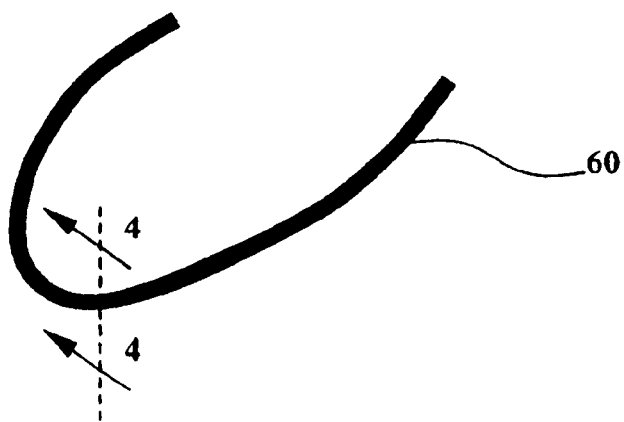
FIG. 3 is a perspective view of an arch wire used for orthodontics.
Figure 4:
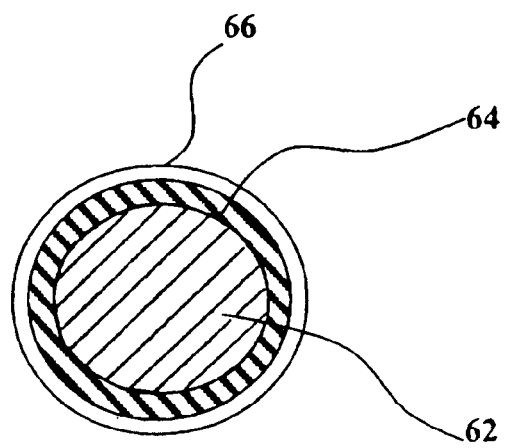
FIG. 4 is a cross-section of the wire of FIG. 3.

As a further example, FIGS. 3 and 4 show another type of orthodontic appliance with which the subject invention can be used, this being an arch wire of the type described in U.S. Pat. No. 4,946,387. The orthodontic arch wire 60 is of general U-shape and comprises a metal wire 62 that illustratively has a circular cross-section. According to the inventive principles, a layer 64 of the coating material containing the antimicrobial agent extends fully circumferentially around wire 62. The coating layer 64 is of circular annular shape so that the resulting overall cross-section of arch wire 60 is of circular shape like wire 62, but slightly larger. The coating 64 containing the antimicrobial agent is formulated and applied as described above.

Wire 62 may be a conventional sized arch wire of typical arch wire metal. The coating 64 can comprise polymeric materials, preferably having elastomeric properties to be able to withstand movement of the arch. This can be a suitable plastic, such as polyethylene or polyurethane, or silicone in which is mixed the particles of the agent. For intra-oral use, silicone is quite inert to chemical influences and it possesses satisfactory abrasion resistance and has good elastomeric properties and will withstand bending of the arch wire. Such materials can be bonded by conventional procedures to the arch wire metal so that they will elongate with the metal when the metal is bent to a desired shape. The coating layer 64 should be thick enough so that the desired effective amount of the agent is present. The antimicrobial agent will be available at all parts of the arch wire to perform its intended function.

A preferred embodiment of the arch wire is:

| | |
|---|---|
| arch wire material | NiTi |
| coating material | acrylic |
| agent type | zeolite silver (e.g. Shinagawa AJ10D) |
| size of agent particles | 1.0 micron |
| wt. % of agent particles in the coating | 55.0% by weight of the coating |

Other types of orthodontic appliances are to have elastomeric, i.e., "rubber-like", properties. These include, for example, elastic bands, elastomeric ligature ties or "threads", elastomeric chains, separators, super ties and Steiner rotation wedges. The invention can be applied to such devices by mixing the agent particles in the polymeric material used to make the appliance. The type of material depends on the appliance. For example, a preferred material for ligature ties is orally acceptable polyether type urethanes. For elastic bands, elastomeric materials such as natural rubber, natural-synthetic rubber, synthetic rubber, certain thermoplastic elastic polymeric materials, and blends thereof are highly preferred. Highly preferred elastomers include natural rubber (polyisoprene), natural-synthetic rubbers, which are generally similar to natural rubber, synthetic rubbers (such as neoprene, butyl and polybutadiene), and blends thereof.

In addition to such rubbers, some specific examples of acceptable elastic polymeric materials are those having polyurethane characteristics, such as a product sold by Dow Chemical Company, Midland, Mich., as PELLATHANE 2363, Mobay Chemical Company, St. Louis, Mo., and plasticized polyethylene.

The choice of a suitable elastic polymeric material will depend on several things, including the orthodontic form or applications and the nature of the agent to be dispersed in it.

As used herein, "polymeric" refers to natural or synthetic materials formed of one or more polymers, that is, organic chemical compounds in which each molecule is made up of simpler molecules strung together. "Elastomer" and "elastic" refers to polymeric materials having rubber-like elastic properties, that is, resilience such that they return to their original shape after stretching or compression. Various methods may be used to make the polymeric elastic orthodontic members incorporating the inorganic agent in accordance with the invention. The choice of an acceptable method will depend in part on the nature of the orthodontic member to be made, that is, whether it is an elastic band, an elastomeric chain, etc.

The process typically involves a blending step in which the antibiotic agent is blended with the orally-acceptable elastic polymeric material. In this step the agent particles or pellets of the particle in a resin base are compounded with the polymeric material such as in a high speed mixer or in a mill with several rollers. The resultant composition is subjected to a heat-forming step, such as extrusion or molding, in which the elastic polymeric material and agent are joined to form a homogenous body of the desired shape or an intermediate shape. In some cases, a final mechanical step, such as cutting, punching, or trimming, may be done to produce the polymeric elastic orthodontic member containing the agent in its final form.

The following are exemplary production processes for the manufacture of elastomeric chains and elastic bands in accordance with this invention.

As with other elastic bands, long elastic tubes of a material containing the agent are first formed and then cut, such as by automatic cutters, to form the bands. For elastomeric chains, flat bands or sheets are first made and then punched and cut to provide the desired form. Other polymeric orthodontic members will be formed with heat-forming steps and, in some cases, later mechanical forming steps as known in the orthodontic implement art.

The long tubes from which elastic bands are cut may be made by a dipping process or an extruding process. In the dipping process, the curing may, for example, be carried out using continuous hot air tunnels or radiant heat. In the extruding process, a hot liquid cure or fluidized bed may be used.

Antimicrobial Agent

The preferred is an inorganic antimicrobial-metal containing composition. Embodiments of the invention described above use ceramic silver zeolite particles. A number of metal ions (cations) have been shown to possess antimicrobial activity, including silver, copper, zinc, mercury, tin, lead, bismuth, cadmium, chromium and thallium ions. These antimicrobial metal ions are believed to exert their effects by disrupting respiration and electron transport systems upon absorption into bacterial or fungal cells. Antimicrobial metal ions of silver, gold, copper and zinc, in particular, are considered safe even for in vivo use. Antimicrobial silver ions are particularly useful for in vivo use due to the fact that they are not substantially absorbed into the body. That is, if such materials are used they should pose no hazard.

In one embodiment of the invention, the inorganic antibiotic metal containing composition is an antibiotic metal salt. Such salts include silver acetate, silver benzoate, silver carbonate, silver ionate, silver iodide, silver lactate, silver laureate, silver nitrate, silver oxide, silver palpitate, silver protein, and silver sulfadiazine. Silver nitrate is preferred. These salts are particularly quick acting, as no release from ceramic particles is necessary to function antimicrobially.

The ceramics employed in the antimicrobial ceramic particles of the present invention include zeolites, hydroxyapatite, zirconium phosphates, or other ion-exchange ceramics. Zeolites are preferred, and are described in the preferred embodiments referred to below. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238, 5,441,717, and 5,405,644.

Inorganic particles, such as the oxides of titanium, aluminum, zinc and copper, may be coated with a composition which confers antimicrobial properties, for example, by releasing antimicrobial metal ions such as silver ions, which are described, e.g., in U.S. Pat. No. 5,189,585. Inorganic soluble glass particles containing antimicrobial metal ions, such as silver, are described, e.g., in U.S. Pat. Nos. 5,766,611 and 5,290,544.

Zeolites

Antimicrobial zeolites have been prepared by replacing all or part of the ion-exchangeable ions in zeolite with ammonium ions and antimicrobial metal ions (cations), as described in U.S. Pat. Nos. 4,938,958 and 4,911,898. Such zeolites have been incorporated in antimicrobial resins (as shown in U.S. Pat. Nos. 4,938,955 and 4,906,464) and polymer articles (U.S. Pat. No. 4,775,585). Polymers including the antimicrobial zeolites have been used to make refrigerators, dish washers, rice cookers, plastic film, chopping boards, vacuum bottles, plastic pails, and garbage containers. Other materials in which antimicrobial zeolites have been incorporated include flooring, wall paper, cloth, paint, napkins, plastic automobile parts, catheters, bicycles, pens, toys, sand, and concrete. Examples of such uses are described in U.S. Pat. Nos. 5,714,445; 5,697,203; 5,562,872; 5,180,585; 5,714,430; and 5,102,401. These applications involve slow release of antimicrobial silver from the zeolite particles.

Antimicrobial ceramic particles useful with the present invention include zeolites, hydroxy apatite, zirconium phosphates or other ion-exchange ceramics. Zeolites are preferred, and are described in the preferred embodiments referred to below. Hydroxy apatite particles containing antimicrobial metals are described, e.g., in U.S. Pat. No. 5,009, 898. Zirconium phosphates containing antimicrobial metals are described, e.g., in U.S. Pat. Nos. 5,296,238; 5,441,717; and 5,405,644.

Antimicrobial zeolites are well-known and can be prepared for use in the present invention using known methods. These include the antimicrobial zeolites disclosed, for example, in U.S. Pat. Nos. 4,938,958 and 4,911,898.

Either natural zeolites or synthetic zeolites can be used to make the antimicrobial zeolites used in the present invention. "Zeolite" is an aluminosilicate having a three dimensional skeletal structure that is represented by the formula: $XM_2/nO—Al_2O_3—YSiO_2—ZH_2O$. M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite= 11.5 meq/g; mordenite=2.6 meq/g; analcite=5 meq/g; clinoptilolite=2.6 meq/g; chabazite=5 meq/g; and erionite= 3.8 meq/g. These ion-exchange capacities are sufficient for the zeolites to undergo ion-exchange with ammonium and antibiotic metal ions.

The specific surface area of preferred zeolite particles is preferably at least 150 m$^2$/g (anhydrous zeolite as standard) and the $SiO_2/Al_2O_3$ mol ratio in the zeolite composition is preferably less than 14, more preferably less than 11.

The antimicrobial metal ions used in the antimicrobial zeolites should be retained on the zeolite particles through an ion-exchange reaction. Antimicrobial metal ions which are adsorbed or attached without an ion-exchange reaction exhibit a decreased bactericidal effect and their antimicrobial effect is not long-lasting. Nevertheless, it is advantageous for imparting quick antimicrobial action to maintain a sufficient amount of surface adsorbed metal ion.

In the ion-exchange process, the antimicrobial metal ions (cations) tend to be converted into their oxides, hydroxides, basic salts etc. either in the micropores or on the surfaces of the zeolite and also tend to deposit there, particularly when the concentration of metal ions in the vicinity of the zeolite surface is high. Such deposition tends to adversely affect the bactericidal properties of ion-exchanged zeolite. This undesirable deposition could be limited to acceptable levels or prevented by adjusting the pH value of the solution to the range of 3 to 10.

In an embodiment of the antibiotic zeolites, a relatively low degree of ion exchange is employed to obtain superior bactericidal properties. It is believed to be required that at least a portion of the zeolite particles should retain metal ions (cations) having bactericidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration, for example 0.3 wt. %, as compared with solutions conventionally used for ion exchange.

In antimicrobial zeolite particles used in the present invention, ion-exchangeable ions present in zeolite, such as sodium ions, calcium ions, potassium ions and iron ions are preferably partially replaced with ammonium and antimicrobial metal ions. Such ions may co-exist in the antimicrobial zeolite particle since they do not prevent the bactericidal effect. While antimicrobial metal ions include ions of silver, copper, zinc, mercury, tin, lead, bismuth, cadmium, chromium and thallium, orally compatible antimicrobial zeolites to be formulated into compositions to be used in the dental appliances of the invention include silver, gold, copper and zinc ions. These antimicrobial metal ions can be used by themselves or in a mixture.

The zeolite preferably comprises an integral discoloration agent such as ion-exchanged ammonium. Although ammonium ions may be contained in the zeolite in an amount as high as about 20% by weight of the zeolite, it is desirable to limit the content of ammonium ions to about 0.5 to about 2.5%, more preferably from about 0.5 to about 2.0%, and most preferably, from about 0.5 to about 1.5% by weight of the zeolite.

The antimicrobial metal ion is preferably present in the range of from about 0.1 to 20.0 wt. % of the zeolite. In one embodiment, the zeolite contain from 0.1 to 20.0 wt. % of silver ions and from 0.1 to 20.0 wt. % of copper or zinc ions. Although ammonium ion can be contained in the zeolite at a concentration of about 20.0 wt. % or less of the zeolite, it is desirable to limit the content of ammonium ions to from 0.5 to 15.0 wt. %, preferably 1.5 to 5.0 wt. %. Weight % described herein is determined for materials dried at temperatures such as 110° C., 250° C. or 550° C. as this is the temperature employed for the preferred post-manufacturing drying process.

A preferred antimicrobial zeolite is type A zeolite containing either a combination of ion-exchanged silver, zinc, and ammonium or silver and ammonium. One such zeolite is manufactured by Shinagawa, Inc. under the product number AW-10N and consists of 0.6% by weight of silver ion-exchanged in Type A zeolite particles having a diameter of about 2.5$\mu$. Another formulation, AJ-10N, consists of about 2% by weight silver ion-exchanged in Type A zeolite particles having a diameter of about 2.5$\mu$. Another formulation, AW-80, contains 0.6% by weight of silver ion-exchanged in Type A zeolite particles having a diameter of about 1.0$\mu$. Another formulation, AJ- 80N, consists of about 2% by weight silver ion-exchanged in Type A zeolite particles having a diameter of about 1.0$\mu$. These zeolites preferably contain about between 0.5% and 2.5% by weight of ion-exchanged ammonium. Other formulations also are available.

The zeolites are often obtained in master batches of low density polyethylene, polypropylene, or polystyrene, containing about 20.0 wt. % of the zeolite. Thus, they can be easily mixed with the resins used as materials for forming the composite resin used to make the dental appliances or in the liquid coating material.

The antibiotic properties of the antibiotic zeolite particles of the invention may be assayed while in aqueous formulations using conventional assay techniques, including for example determining the minimum growth inhibitory content (MIC) with respect to a variety of bacteria, eumycetes and yeast. In such a test, the bacteria listed below may be employed:
*Bacillus cereus varmycoides;*
*Escherichia coli;*
*Pseudomonas aeruginosa;*

*Staphylococcus aureus;*
*Streptococcus mutans;*
*Aspergillus niger;*
*Aureobasidium pullulans;*
*Chaetomium globosum;*
*Gliocladium virens;*
*Penicillum funiculosum;*
*Candida albicans;* and
*Saccharomyces cerevisiae.*

The assay for determining MIC can be carried out by smearing a solution containing bacteria for inoculation onto a plate culture medium to which a test sample of the encapsulated antibiotic zeolite particles is added in a particular concentration, followed by incubation and culturing of the plate. The MIC is defined as a minimum content thereof required for inhibiting the growth of each bacteria.

Safety and biocompatibility tests were conducted on the antibiotic zeolites employed in the invention. ISO 10993-1 procedures were employed. The following results were obtained:
Cytotoxicity: Non-Toxic
Acute Systemic Toxicity: Non-Toxic
Oral Toxicity: Safer than table salt
Intracutaneous Toxicity: Passed
Skin Irritation Test: Non-Irritant
Chronic Toxicity: No Observable Effect
In-vitro Hemolysis: Non-Hemolytic
30-day Muscle Implant Test: Passed
60-day Muscle Implant Test: Passed
90-day Muscle Implant Test: Passed
Ames Mutagenicity Test: Passed
Pyrogenicity: Non-Pyrogenic Thus, the antimicrobial zeolites are exceptionally suitable under relevant toxicity and biocompatibility standards for use in the dental appliances.

Specific features of the invention are shown in one or more of the drawings for convenience only, as each feature may be combined with other features in accordance with the invention. Alternative embodiments will be recognized by those skilled in the art and are intended to be included within the scope of the claims.

We claim:

1. A dental appliance comprising a polymeric material incorporating ceramic particles with one or more antibiotic metal cations ion-exchanged thereon, wherein some or all of the ceramic particles are exposed to a surface of the polymeric material, such that upon placement into the mouth of a subject, water and cations can enter the exposed ceramic particles and effect an ion-exchange reaction to release an antimicrobially effective amount of antibiotic metal cations from the dental appliance.

2. The dental appliance of claim 1 wherein the ceramic particles are selected from the group consisting of zeolite, hydroxy apatite, and zirconium phosphate.

3. The dental appliance of claim 1 wherein the ceramic particles are antibiotic zeolite particles prepared by replacing all or part of the ion-exchangeable ions of the zeolite with antimicrobial silver cations.

4. The dental appliance of claim 3 wherein the zeolite particles have a diameter between about 0.5 and 3.0 microns.

5. The dental appliance of claim 3 wherein the zeolite particles constitute between about 0.1 to 5.0 percent of the total weight of the polymeric material.

6. The dental appliance of claim 1 wherein the polymeric material is a coating comprising the ceramic particles.

7. The dental appliance of claim 6 wherein the coating is on a metal substrate.

8. The dental appliance of claim 6 wherein the ceramic particles constitute 0.5 to 50.0% of the total weight of the coating.

9. The dental appliance of claim 1 wherein the polymeric material comprises an elastomeric material.

10. The dental appliance of claim 1 wherein the polymeric material comprises polycarbonate.

11. The dental appliance of claim 1 which is a dental bracket.

12. The dental appliance of claim 1 which is an arch wire.

13. A dental appliance comprising a metal at least partially coated with a polymeric material incorporating ceramic particles with one or more antibiotic metal cations ion-exchanged thereon, wherein some or all of the ceramic particles are exposed to a surface of the polymeric material, such that upon placement into the mouth of a subject, water and cations can enter the material and effect an ion-exchange reaction to release an antimicrobially effective amount of antibiotic metal cations from the dental appliance.

14. The dental appliance of claim 13 wherein the ceramic particles are selected from the group consisting of zeolite, hydroxy apatite, and zirconium phosphate.

15. The dental appliance of claim 13 wherein the ceramic particles are antibiotic zeolite particles prepared by replacing all or part of the ion-exchangeable ions of the zeolite with antimicrobial silver cations.

16. The dental appliance of claim 15 wherein the zeolite particles have a diameter between about 0.5 and 3.0 microns.

17. The dental appliance of claim 15 wherein the ceramic particles constitute between about 0.1 to 5.0 percent of the total weight of the polymeric material.

18. The dental appliance of claim 13 wherein the polymeric material comprises a polycarbonate.

19. The dental appliance of claim 13 wherein the polymeric material further comprises a colorant.

20. The dental appliance of claim 13 which is a dental bracket.

21. The dental appliance of claim 13 which is an arch wire.

* * * * *